United States Patent [19]

Boudakian

[11] 4,008,278
[45] Feb. 15, 1977

[54] PREPARATION OF 2-AMINO-5-HALOBENZOTRIFLUORIDE

[75] Inventor: Max M. Boudakian, Pittsford, N.Y.

[73] Assignee: Olin Corporation, New Haven, Conn.

[22] Filed: Sept. 4, 1975

[21] Appl. No.: 610,130

[52] U.S. Cl. .................... 260/578; 260/562 R
[51] Int. Cl.² .................. C07C 87/60; C07C 85/24
[58] Field of Search .................... 260/578, 562 R

[56] References Cited

UNITED STATES PATENTS

| | | | |
|---|---|---|---|
| 1,698,884 | 1/1929 | Hoffa et al. | 260/578 X |
| 1,930,754 | 10/1933 | Havas et al. | 260/578 X |
| 2,031,666 | 2/1936 | Perkins | 260/578 |
| 2,056,899 | 10/1936 | Hoffa et al. | 260/578 |
| 2,093,115 | 9/1937 | Wolfram et al. | 260/578 |
| 2,194,926 | 3/1940 | Daudt et al. | 260/578 |
| 2,733,269 | 1/1956 | Raimond et al. | 260/578 |
| 3,453,335 | 7/1969 | Starnes, Jr. | 260/578 X |
| 3,890,388 | 6/1975 | Schimelpfenig | 260/578 |

OTHER PUBLICATIONS

Tarrant et al., CA 49:5340b (1954).

*Primary Examiner*—Daniel E. Wyman
*Assistant Examiner*—Thomas A. Waltz
*Attorney, Agent, or Firm*—F. A. Iskander; T. P. O'Day

[57] ABSTRACT

2-Amino-5-halobenzotrifluorides are prepared to the virtual exclusion of other monohalogenated isomers by halogenating an aminobenzotrifluoride with a hydrohalide acid in the presence of selected oxidants.

6 Claims, No Drawings

PREPARATION OF 2-AMINO-5-HALOBENZOTRIFLUORIDE

Direct chlorination of o-aminobenzotrifluoride has been attempted in assorted solvent systems in accordance with the equation:

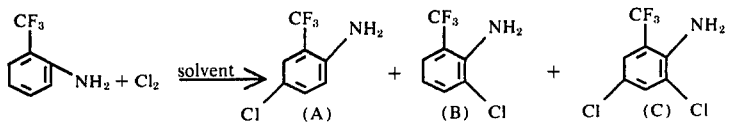

BACKGROUND

1. Field of Invention

The present invention relates to a process for halogenating aminobenzotrifluorides to produce 2-amino-5-halobenzotrifluoride to the virtual exclusion of other monohalogenated isomers.

2. Prior Art

2-Amino-5-chlorobenzotrifluoride is employed commercially as a dye intermediate. The treatise, Colour Index, Chemical No. 37055, Vol. 1–4, 2nd ed., 1956, Suppl. 1963, published by the Society of Dyers and Colourists (U.K.) and the American Association of Textile Chemists and Colorists (U.S.) designates this material as C.I. Azoic Diazo Component 17. It is known to couple this compound with Naphthol A.S. to produce a fade resistant red dye having the formula:

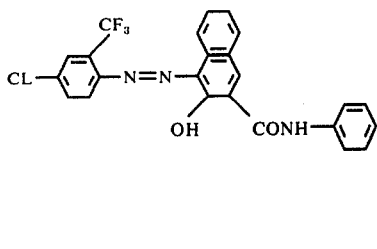

Colour Index, supra, indicates that 2-amino-5-chlorobenzotrifluoride is prepared commercially by the successive nitration-reduction of m-chlorobenzotrifluoride. The desired isomer is separated by freezing or other suitable means from the resulting undesired isomers and then reduced. The isomeric separation, regardless of the method employed is expensive and renders the overall process commercially unacceptable.

Whalley, J. Chem. Soc., 3016 (1949) described a process for preparing 2-amino-5-chlorobenzotrifluoride from m-aminobenzotrifluoride by acetylating to form the acetanilide derivative, then nitrating to form a 2-nitro-5-aminobenzotrifluoride, chlorinating with sodium nitrite and HCl in the presence of cuprous chloride and finally reducing the resulting nitro to an amino group. This process is a multi-step process involving at least 4 major steps.

2-Amino-5-chlorobenzotrifluoride has been prepared from N-(2-trichloromethyl-4-chlorophenyl) phthalimide by exchange fluorination with HF followed by hydrolysis as disclosed in French Patent 805,704 (1936), British Patent 459,890 (1937) and C.A., 31 4342 (1973). E. J. Forbes et al., Tetrahedron, 8 67 (1960) reports low yields by this route.

The solvents utilized include water, aqueous acetic acid, aqueous hydrochloric acid and methanol. While products A and B are readily separable, the quantity of B produced varied from 14–25% of total product. Since there is no known use for this by-product, its production represents a substantial economic loss.

SUMMARY OF THE INVENTION

It has now been found that 2-amino-5-halobenzotrifluorides are readily formed to the virtual exclusion of other monohalogenated products by reacting a selected aminobenzotrifluoride with a suitable halogen source in the presence of a selected oxidant, thus avoiding the necessity for lengthy multi-step processes and also avoiding the economic loss encountered in the production of substantial amounts of undesired monohalogenated species.

DETAILED DESCRIPTION

The present invention comprises a one-step chlorination process which may be represented by the general equation:

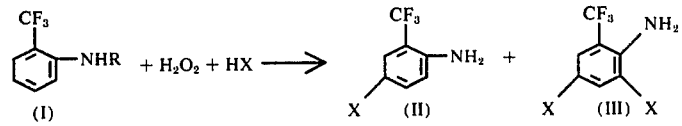

wherein R is a hydrogen, acetyl or formyl group and X is a halogen selected from the group consisting of chlorine, bromine and iodine, and $H_2O_2$ is the selected oxidant.

The starting reactant is an aminobenzotrifluoride which may be selected from the group consisting of o-aminobenzotrifluoride, o-acetaminobenzotrifluoride and o-formylaminobenzotrifluoride.

A suitable halogen source includes hydrohalide acids including hydrochloric acid, hydrobromic acid or hydroiodic acid depending on which halogen is to be substituted on the aromatic nucleus. At least one mole of the selected hydrohalide acid suitably 1–20 and preferably 2–10 are employed per mole of the aminobenzotrifluoride starting reactant. The halogen source material is preferably an aqueous solution but anhydrous material may also be utilized.

At least one mole of oxidant per mole of the aminobenzotrifluoride is advantageously employed but as little as 0.5 mole up to about 10 moles per mole of the aminobenzotrifluoride may be employed if desired with the preferred range being from about 0.75 to about 5 moles per mole of the aminobenzotrifluoride. While the preferred oxidant is hydrogen peroxide, other suitable oxidants include sodium peroxide, potassium chlorate, potassium bromate and potassium permanganate.

The reaction is suitably conducted in aqueous solution at a temperature in the range of 10° C up to about 100° C, preferably ambient up to about 100° C. The reaction is exothermic resulting in an autogeneous rise in temperature during the reaction. Suitably, the exotherm may be controlled in any convenient manner to maintain the temperature below the boiling point of the reaction mixture to avoid the need for condensers and/or high pressure equipment.

In the preferred embodiment hereof the aminobenzotrifluoride starting reactant is dissolved in an aqueous solution of the hydrohalide acid or in water and the hydrohalide acid added prior to addition of the oxidant. The oxidant is then added slowly, preferably dropwise until addition is completed. As the oxidant is added to the mixture, nascent halogen is released and reacts with the benzotrifluoride. Following completion of oxidant addition the reaction is allowed to stand for a suitable post addition reaction period, suitably 5 minutes to 5 hours and is preferably maintained at or about the final temperature during this period.

It is apparent that the reaction may also be conducted by suitably modifying the addition sequence of the preferred embodiment, for example, by adding hydrohalide acid and oxidant simultaneously to an aqueous mixture of the aminobenzotrifluoride or to an aqueous mixture of the aminobenzotrifluoride and oxidant, without departing from the spirit and scope of the present invention.

The following examples further illustrate the method of the present invention.

EXAMPLE 1

$H_2O_2$/HCl Chlorination System

An aqueous solution of o-aminobenzotrifluoride hydrochloride was prepared by the addition of o-aminobenzotrifluoride (1 mole; 161.1 grams) to 37% hydrochloric acid (10.8 moles; 1232 grams) at 24° C–36° C. Hydrogen peroxide (35.3%; 1.18 moles; 113.7 grams) was added dropwise over a 0.5 hour period (initial temp., 29° C; final temp. 81° C) and then maintained at 70° C–80° C for an additional 0.5 hour period. The acidic solution was neutralized with 50% sodium hydroxide (pH 10) and the contents steam distilled to give 198.0 grams of an organic product, wt. 198.0 grams.

VPC assay of the organic product revealed the following composition (15% XE 60 column packing; 120° C–250° C; 4°/min.): o-aminobenzotrifluoride (13.1 wt. %; 25.94 grams; 0.161 mole; 83.9% conversion); 2-amino-5-chlorobenzotrifluoride, 53.5 wt. %; 105.9 grams or 64.5% corrected yield); and, 2-amino-3,5-dichlorobenzotrifluoride, 33.3 wt. %; 65.93 grams or 34.2% corrected yield). A trace of 2-amino-3-chlorobenzotrifluoride was produced.

EXAMPLE 2

$Cl_2$/$H_2O$ System

Chlorine (88 grams, 1.22 moles) was introduced to a mixture of o-aminobenzotrifluoride (196 grams, 1.22 moles) and water (600 grams) at 20°–40° C. The reaction mixture was neutralized with 29% ammonium hydroxide (73 grams, 1.24 moles) and the lower organic layer phased. The aqueous phase was extracted once with methylene chloride (500 grams). The combined organic layer and methylene chloride extract was treated with anhydrous hydrogen chloride (29 grams, 0.784 mole). The precipitated solids were filtered and washed with 100 grams methylene chloride.

The combined hydrochloride salts of o-aminobenzotrifluoride and 2-amino-5-chlorobenzotrifluoride were dispersed in 300 grams water and neutralized with 46 grams (0.784 mole) of 29% ammonium hydroxide. The organic layer was drawn off and vacuum-distilled giving o-aminobenzotrifluoride (b.p. 47.5° C/6 mm.; 44 grams; 0.273 mole; conversion 77%) and 2-amino-5-chlorobenzotrifluoride (b.p. 49° C/1 mm.; 100 grams; 0.511 mole; 54% corrected yield).

The methylene chloride solution from filtration of the hydrochloride salts was stripped of solvent and vacuum distilled giving 2-amino-3-chlorobenzotrifluoride (b.p. 47° C/3.5 mm.; 46 grams; 0.235 mole; 25% corrected yield) and 2-amino-3,5-dichlorobenzotrifluoride (b.p. 64° C/1.9 mm.; 45 grams; 0.196 mole; 21% corrected yield).

EXAMPLES 3–5

The procedure of Example 2 was repeated but varying the chlorination system. The chlorination system, temperature conversion of o-aminobenzotrifluoride and corrected yield of the various isomers is shown in Table I together with the results of Examples 1 and 2. Isomer I is 2-amino-5-chlorobenzotrifluoride, the desired product, II is 2-amino-3-chlorobenzotrifluoride, the undesired isomer and III is the 2-amino-3,5-dichlorobenzotrifluoride.

TABLE I

| Example | Chlorination System | Temp. °C | Conversion OABTF* | Corrected Yield I | II | III |
|---|---|---|---|---|---|---|
| 1 | $H_2O_2$/HCl | 24–80 |  | 64.5 | Tr. | 34.2 |
| 2 | $Cl_2$/$H_2O$ | 20–40 | 77 | 54 | 25 | 21 |
| 3 | $Cl_2$/$CH_3CO_2H$ | 40–50 | 52 | 59 | 14 | 27 |
| 4 | $Cl_2$/$H_2O$/HCl | 5–10 | 67 | 66 | 14 | 20 |
| 5 | $Cl_2$/$CH_3OH$ | 40–50 | 79 | 54 | 15 | 31 |

*o-aminobenzotrifluoride

What is claimed is:

1. An improved process for preparing 2-amino-5-halobenzotrifluoride comprising
    reacting an aminobenzotrifluoride selected from the group consisting of o-aminobenzotrifluoride, o-acetaminobenzotrifluoride, and o-formylaminobenzotrifluoride with a halogen source selected from the group consisting of hydrochloric, hydrobromic and hydroiodic acid in the presence of an oxidant selected from the group consisting of hydrogen peroxide, sodium peroxide, potassium chlorate, potassium bromate and potassium permanganate to produce a product consisting essentially of said 2-amino-5-halobenzotrifluoride.

2. The process of claim 1 wherein said oxidant is hydrogen peroxide.

3. The process of claim 2 wherein said reaction is conducted at a temperature in the range of 20° C–100° C.

4. The process of claim 3 wherein the molar ratio of said halogen source to said aminobenzotrifluoride is from 2:1 to 20:1.

5. The process of claim 1 wherein a molar excess of said halogen source is employed.

6. The process of claim 5 wherein said oxidant is added slowly to an aqueous solution of said benzotrifluoride and said halogen source.

* * * * *